(12) United States Patent
Stahl et al.

(10) Patent No.: US 7,083,950 B2
(45) Date of Patent: Aug. 1, 2006

(54) HIGH AFFINITY FUSION PROTEINS AND THERAPEUTIC AND DIAGNOSTIC METHODS FOR USE

(75) Inventors: Neil Stahl, Carmel, NY (US); George D. Yancopoulos, Yorktown Heights, NY (US); Margaret Karow, Putnam Valley, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 324 days.

(21) Appl. No.: 10/610,452

(22) Filed: Jun. 30, 2003

(65) Prior Publication Data

US 2005/0074855 A1 Apr. 7, 2005

Related U.S. Application Data

(63) Continuation-in-part of application No. 09/787,835, filed as application No. PCT/US99/22045 on Sep. 22, 1999, now abandoned, which is a continuation-in-part of application No. 09/313,942, filed on May 19, 1999, now Pat. No. 6,472,179.

(60) Provisional application No. 60/101,858, filed on Sep. 25, 1998.

(51) Int. Cl.
*C12P 21/04* (2006.01)
*C07H 21/04* (2006.01)

(52) U.S. Cl. .................. 435/69.7; 530/350; 530/387.3; 530/388.2; 435/320; 435/325; 536/23.4; 536/23.5; 514/2; 424/192.1

(58) Field of Classification Search ............. None
See application file for complete search history.

(56) References Cited

U.S. PATENT DOCUMENTS

| 5,480,982 A | * | 1/1996 | Sugita et al. ............ 536/26.24 |
| 5,597,710 A | * | 1/1997 | Dalie et al. ................ 435/69.6 |
| 6,121,424 A | * | 9/2000 | Whitlow et al. ......... 530/387.3 |
| 6,793,919 B1 | | 9/2004 | Mohler |

FOREIGN PATENT DOCUMENTS

WO WO96/37621 11/1996

OTHER PUBLICATIONS

Lu, et al (2001) Cancer Research, 61:7002-7008.
Zuo, et al. (2000) Protein Engineering, 13:361-367.
Alt, et al. (1999) FEBS Lett., 454:90-94.
Muller, et al., (1998) FEBS Lett. 432:45-49.
Connelly, et al. (1998) Intl. Immun. 10:1863-1872.
Neri, et al. (1995) J. Mol. Biol. 246:367-373.
Pereboev, et al. (2002) Gene Terapy 9:1189-1193.

* cited by examiner

*Primary Examiner*—Eileen B. O'Hara
(74) *Attorney, Agent, or Firm*—Valeta Gregg, Esq.

(57) ABSTRACT

High affinity fusion proteins ("trapbodies"), capable of binding and inhibiting the activity of soluble, interacting proteins ("SIPs") are described. The trapbodies are multimers, preferably dimers, of SIP-specific fusion polypeptides which comprise SIP binding domains derived from SIP targets and/or anti-SIP immunoglobulins, as well as multimerizing components.

14 Claims, No Drawings

SEQUENCE LISTING

<160> NUMBER OF SEQ ID NOS: 17

<210> SEQ ID NO 1
<211> LENGTH: 45
<212> TYPE: DNA
<213> ORGANISM: Artificial Sequence
<220> FEATURE:
<223> OTHER INFORMATION: linker

<400> SEQUENCE: 1
ggtggaggcg gttcaggcgg aggtggctct ggcggtggcg gatcg          45

<210> SEQ ID NO 2
<211> LENGTH: 15
<212> TYPE: PRT
<213> ORGANISM: Artificial Sequence
<220> FEATURE:
<223> OTHER INFORMATION: linker

<400> SEQUENCE: 2

Gly Gly Gly Gly Ser Gly Gly Gly Gly Ser Gly Gly Gly Gly Ser
 1               5                  10                  15

<210> SEQ ID NO 3
<211> LENGTH: 936
<212> TYPE: DNA
<213> ORGANISM: homo sapiens

<400> SEQUENCE: 3
actgcggaat cttgtacttc acgtccccac attactgtgg ttgaagggga acctttctat     60
ctgaaacatt gctcgtgttc acttgcacat gagattgaaa caaccaccaa aagctggtac    120
aaaagcagtg gatcacagga acatgtggag ctgaacccaa ggagttcctc gagaattgct    180
ttgcatgatt gtgttttgga gttttggcca gttgagttga atgacacagg atcttacttt    240
ttccaaatga aaaattatac tcagaaatgg aaattaaatg tcatcagaag aaataaacac    300
agctgtttca ctgaaagaca gtaactagt aaaattgtgg aagttaaaaa atttttttcag    360 ataacctgtg aaaacagtta ctatcaaaca ctggtcaaca gcacatcatt gtataagaac    420
tgtaaaaagc tactactgga gaacaataaa aacccaacga taaagaagaa cgccgagttt    480
gaagatcagg ggtattactc ctgcgtgcat ttccttcatc ataatggaaa actatttaat    540
atcaccaaaa ccttcaatat aacaatagtg gaagatcgca gtaatatagt tccggttctt    600
cttggaccaa agcttaacca tgttgcagtg gaattaggaa aaaacgtaag gctcaactgc    660
tctgctttgc tgaatgaaga ggatgtaatt tattggatgt tcgggggaaga aaatggatcg    720 gatcctaata tacatgaaga gaaagaaatg agaattatga ctccagaagg caaatggcat    780
gcttcaaaag tattgagaat tgaaaatatt ggtgaaagca atctaaatgt tttatataat    840
tgcactgtgg ccagcacggg aggcacagac accaaaagct tcatcttggt gagaaaagca    900
gacatggctg atatcccagg ccacgtcttc acaaga                               936

<210> SEQ ID NO 4
<211> LENGTH: 312
<212> TYPE: PRT
<213> ORGANISM: homo sapiens

<400> SEQUENCE: 4

Thr Ala Glu Ser Cys Thr Ser Arg Pro His Ile Thr Val Val Glu Gly
 1               5                  10                  15

-continued

```
Glu Pro Phe Tyr Leu Lys His Cys Ser Cys Ser Leu Ala His Glu Ile
             20                  25                  30
Glu Thr Thr Thr Lys Ser Trp Tyr Lys Ser Ser Gly Ser Gln Glu His
         35                  40                  45
Val Glu Leu Asn Pro Arg Ser Ser Arg Ile Ala Leu His Asp Cys
     50                  55                  60
Val Leu Glu Phe Trp Pro Val Glu Leu Asn Asp Thr Gly Ser Tyr Phe
 65                  70                  75                  80
Phe Gln Met Lys Asn Tyr Thr Gln Lys Trp Lys Leu Asn Val Ile Arg
                 85                  90                  95
Arg Asn Lys His Ser Cys Phe Thr Glu Arg Gln Val Thr Ser Lys Ile
             100                 105                 110
Val Glu Val Lys Lys Phe Phe Gln Ile Thr Cys Glu Asn Ser Tyr Tyr
         115                 120                 125
Gln Thr Leu Val Asn Ser Thr Ser Leu Tyr Lys Asn Cys Lys Lys Leu
     130                 135                 140
Leu Leu Glu Asn Asn Lys Asn Pro Thr Ile Lys Lys Asn Ala Glu Phe
145                 150                 155                 160
Glu Asp Gln Gly Tyr Tyr Ser Cys Val His Phe Leu His His Asn Gly
                 165                 170                 175
Lys Leu Phe Asn Ile Thr Lys Thr Phe Asn Ile Thr Ile Val Glu Asp
             180                 185                 190
Arg Ser Asn Ile Val Pro Val Leu Leu Gly Pro Lys Leu Asn His Val
         195                 200                 205
Ala Val Glu Leu Gly Lys Asn Val Arg Leu Asn Cys Ser Ala Leu Leu
     210                 215                 220
Asn Glu Glu Asp Val Ile Tyr Trp Met Phe Gly Glu Glu Asn Gly Ser
225                 230                 235                 240
Asp Pro Asn Ile His Glu Glu Lys Glu Met Arg Ile Met Thr Pro Glu
                 245                 250                 255
Gly Lys Trp His Ala Ser Lys Val Leu Arg Ile Glu Asn Ile Gly Glu
             260                 265                 270
Ser Asn Leu Asn Val Leu Tyr Asn Cys Thr Val Ala Ser Thr Gly Gly
         275                 280                 285
Thr Asp Thr Lys Ser Phe Ile Leu Val Arg Lys Ala Asp Met Ala Asp
     290                 295                 300
Ile Pro Gly His Val Phe Thr Arg
305                 310

<210> SEQ ID NO 5
<211> LENGTH: 708
<212> TYPE: DNA
<213> ORGANISM: homo sapiens

<400> SEQUENCE: 5
gagatccagc tgcagcagtc tggacctgag ctggtgaagc ctggggcttc agtgaaggtc      60
tcctgtaagg cttctggtta ctcattcact gactacttca tttactgggt gaagcagagc     120
catggaaaga gccttgagtg gattggagat attgatcctt ataatggtga tactagttac     180
aaccagaagt tcaggacaa ggccacattg actgttgacc agtcctccac cacagccttc     240
atgcatctca acagcctgac atctgaggac tctgcagtct atttctgtgc aagaggccta     300
cggttctggg gccaagggac tctggtcact gtctctgcag gtggaggcgg ttcaggcgga     360
ggtggctctg gcggtggcgg atcggacatc cagatgaccc agtctccatc ctccttatct     420
```

```
gcctctctgg gagaaagagt cagtctcact tgtcgggcaa gtcaggacat tggtagtaaa    480
ttatactggc ttcaacagga accagatgga acttttaaac gcctgatcta cgccacatcc    540
agtttagatt ctggtgtccc caagaggttc agtggcagta ggtctgggtc agattattct    600
ctcaccatca gcagccttga gtctgaagat tttgtagact attactgtct acaatatgct    660
agttctccgt acacgttcgg agggggacc aagctggcaa taaaacgg                  708
```

<210> SEQ ID NO 6
<211> LENGTH: 236
<212> TYPE: PRT
<213> ORGANISM: homo sapiens

<400> SEQUENCE: 6

```
Glu Ile Gln Leu Gln Gln Ser Gly Pro Glu Leu Val Lys Pro Gly Ala
  1               5                  10                  15

Ser Val Lys Val Ser Cys Lys Ala Ser Gly Tyr Ser Phe Thr Asp Tyr
                 20                  25                  30

Phe Ile Tyr Trp Val Lys Gln Ser His Gly Lys Ser Leu Glu Trp Ile
             35                  40                  45

Gly Asp Ile Asp Pro Tyr Asn Gly Asp Thr Ser Tyr Asn Gln Lys Phe
         50                  55                  60

Arg Asp Lys Ala Thr Leu Thr Val Asp Gln Ser Ser Thr Thr Ala Phe
 65                  70                  75                  80

Met His Leu Asn Ser Leu Thr Ser Glu Asp Ser Ala Val Tyr Phe Cys
                 85                  90                  95

Ala Arg Gly Leu Arg Phe Trp Gly Gln Gly Thr Leu Val Thr Val Ser
                100                 105                 110

Ala Gly Gly Gly Gly Ser Gly Gly Gly Gly Ser Gly Gly Gly Gly Ser
            115                 120                 125

Asp Ile Gln Met Thr Gln Ser Pro Ser Ser Leu Ser Ala Ser Leu Gly
        130                 135                 140

Glu Arg Val Ser Leu Thr Cys Arg Ala Ser Gln Asp Ile Gly Ser Lys
145                 150                 155                 160

Leu Tyr Trp Leu Gln Gln Glu Pro Asp Gly Thr Phe Lys Arg Leu Ile
                165                 170                 175

Tyr Ala Thr Ser Ser Leu Asp Ser Gly Val Pro Lys Arg Phe Ser Gly
            180                 185                 190

Ser Arg Ser Gly Ser Asp Tyr Ser Leu Thr Ile Ser Ser Leu Glu Ser
        195                 200                 205

Glu Asp Phe Val Asp Tyr Tyr Cys Leu Gln Tyr Ala Ser Ser Pro Tyr
    210                 215                 220

Thr Phe Gly Gly Gly Thr Lys Leu Ala Ile Lys Arg
225                 230                 235
```

<210> SEQ ID NO 7
<211> LENGTH: 690
<212> TYPE: DNA
<213> ORGANISM: homo sapiens

<400> SEQUENCE: 7

```
tccggagaca aaactcacac atgcccaccg tgcccagcac ctgaactcct ggggggaccg     60
tcagtcttcc tcttcccccc aaaacccaag gacaccctca tgatctcccg gacccctgag    120
gtcacatgcg tggtggtgga cgtgagccac gaagaccctg aggtcaagtt caactggtac    180
gtggacggcg tggaggtgca taatgccaag acaaagccgc gggaggagca gtacaacagc    240
```

```
acgtaccgtg tggtcagcgt cctcaccgtc ctgcaccagg actggctgaa tggcaaggag      300
tacaagtgca aggtctccaa caaagccctc ccagccccca tcgagaaaac catctccaaa      360 gccaagggc agccccgaga accacaggtg tacaccctgc cccatcccg ggatgagctg        420 accaagaacc aggtcagcct gacctgcctg gtcaaaggct tctatcccag cgacatcgcc      480
gtggagtggg agagcaatgg gcagccggag aacaactaca agaccacgcc tcccgtgctg      540
gactccgacg gctccttctt cctctatagc aagctcaccg tggacaagag caggtggcag      600
caggggaacg tcttctcatg ctccgtgatg catgaggctc tgcacaacca ctacacgcag      660
aagagcctct ccctgtctcc gggtaaatga                                       690
```

<210> SEQ ID NO 8
<211> LENGTH: 229
<212> TYPE: PRT
<213> ORGANISM: homo sapiens

<400> SEQUENCE: 8

```
Ser Gly Asp Lys Thr His Thr Cys Pro Pro Cys Pro Ala Pro Glu Leu
  1               5                  10                  15

Leu Gly Gly Pro Ser Val Phe Leu Phe Pro Pro Lys Pro Lys Asp Thr
             20                  25                  30

Leu Met Ile Ser Arg Thr Pro Glu Val Thr Cys Val Val Val Asp Val
         35                  40                  45

Ser His Glu Asp Pro Glu Val Lys Phe Asn Trp Tyr Val Asp Gly Val
     50                  55                  60

Glu Val His Asn Ala Lys Thr Lys Pro Arg Glu Glu Gln Tyr Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Asp Glu Leu Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Pro Gly Lys
225
```

<210> SEQ ID NO 9
<211> LENGTH: 729
<212> TYPE: DNA
<213> ORGANISM: homo sapiens

<400> SEQUENCE: 9

```
caggtccagc ttcagcagtc tggggctgaa ctggcaaaac ctggggcctc agtgaagatg       60
```

-continued

```
tcctgcaagg cttctggcta cacctttact acctactgga tgcactggat aaaacagagg    120
cctggacagg gtctggaatg gattggatac attaatccta gtactggtta ttctgagttc    180
aatcagaagt tcaatgacaa ggccacattg actgcagaca atcctccag tacagcctac     240 atgcaactga acagcctgac atctgaagac tctgcagtct attactgtgc aagagatgcc    300
tactatggta actacgaaga ctattgggc caaggcacca ctctcacagt ctcctcagcc     360
ggtggaggcg gttcaggcgg aggtggctct ggcggtggcg gatcgagtat tgtgatgacc    420
cagactccca aattcctgct tgtatcagca ggagacaggg ttaccataac ctgcaaggcc    480
agtcagagtg tgagttatga tgtagcttgg taccaacaga gccagggca gtctccaaaa    540 ctgctgatat actatgaatc caatcgctat agtggagtcc ctgatcgctt cactggcagt    600
ggaaatggga cggatttcac tttcaccatc agcactgtgc aggctgaaga cctggcagtt    660
tatttctgtc agcaggttta tacctctccg tacacgttcg gagggggac caagctggaa    720 ataaaacgg                                                           729
```

<210> SEQ ID NO 10
<211> LENGTH: 243
<212> TYPE: PRT
<213> ORGANISM: homo sapiens

<400> SEQUENCE: 10

```
Gln Val Gln Leu Gln Gln Ser Gly Ala Glu Leu Ala Lys Pro Gly Ala
  1               5                  10                  15

Ser Val Lys Met Ser Cys Lys Ala Ser Gly Tyr Thr Phe Thr Thr Tyr
             20                  25                  30

Trp Met His Trp Ile Lys Gln Arg Pro Gly Gln Gly Leu Glu Trp Ile
         35                  40                  45

Gly Tyr Ile Asn Pro Ser Thr Gly Tyr Ser Glu Phe Asn Gln Lys Phe
     50                  55                  60

Asn Asp Lys Ala Thr Leu Thr Ala Asp Arg Ser Ser Ser Thr Ala Tyr
 65                  70                  75                  80

Met Gln Leu Asn Ser Leu Thr Ser Glu Asp Ser Ala Val Tyr Tyr Cys
                 85                  90                  95

Ala Arg Asp Ala Tyr Tyr Gly Asn Tyr Glu Asp Tyr Trp Gly Gln Gly
            100                 105                 110

Thr Thr Leu Thr Val Ser Ser Ala Gly Gly Gly Ser Gly Gly Gly
        115                 120                 125

Gly Ser Gly Gly Gly Gly Ser Ser Ile Val Met Thr Gln Thr Pro Lys
    130                 135                 140

Phe Leu Leu Val Ser Ala Gly Asp Arg Val Thr Ile Thr Cys Lys Ala
145                 150                 155                 160

Ser Gln Ser Val Ser Tyr Asp Val Ala Trp Tyr Gln Gln Lys Pro Gly
                165                 170                 175

Gln Ser Pro Lys Leu Leu Ile Tyr Tyr Glu Ser Asn Arg Tyr Ser Gly
            180                 185                 190

Val Pro Asp Arg Phe Thr Gly Ser Gly Asn Gly Thr Asp Phe Thr Phe
        195                 200                 205

Thr Ile Ser Thr Val Gln Ala Glu Asp Leu Ala Val Tyr Phe Cys Gln
    210                 215                 220

Gln Val Tyr Thr Ser Pro Tyr Thr Phe Gly Gly Gly Thr Lys Leu Glu
225                 230                 235                 240

Ile Lys Arg
```

<210> SEQ ID NO 11
<211> LENGTH: 729
<212> TYPE: DNA
<213> ORGANISM: homo sapiens

<400> SEQUENCE: 11

```
gaaatgaaac ttgaggagtc tggaggaggc ttggtgcaac ctggaggatc catgaaactc     60
tcttgtgctg cctctggatt cacttttagt gacgcctgga tggactgggt ccgccagtct    120
ccagagaagg ggcttgagtg ggttgctgaa attagaagca aagctaaaga tcatgcaaca    180
tactatgctg agtctgtgaa agggaggttc accatctcaa gagatgattc caagagtagt    240
gtctacctgc aaatgaacag tttaagagct gaagacactg gcattttatta ctgtaccagg    300
gggagctcac gctggggtca aggaacctca gtcaccgtct cctcagccgg tggaggcggt    360
tcaggaggag gtggctctgg cggtggcgga tcggacattg tgctgacaca gtctcctgct    420
tccttagctg tatctctggg gcagagggcc accatctcat gcagggccag ccaaagtgtc    480
agtacatcta cctatagtta tatgcactgg taccaacaga aaccaggaca gccacccaaa    540
ctcctcatca gtatgcatc aacctagaa tccggggtcc ctgccaggtt cagtggcagt    600
gggtctggga cagacttcac cctcaacatc catcctgtgg aggaggagga tactgcaaca    660
tattactgtc agcaggcttg ggagattccg tggacgttcg gtggaggcac cacgctggaa    720
atcagacgg                                                           729
```

<210> SEQ ID NO 12
<211> LENGTH: 243
<212> TYPE: PRT
<213> ORGANISM: homo sapiens

<400> SEQUENCE: 12

```
Glu Met Lys Leu Glu Glu Ser Gly Gly Gly Leu Val Gln Pro Gly Gly
  1               5                  10                  15

Ser Met Lys Leu Ser Cys Ala Ala Ser Gly Phe Thr Phe Ser Asp Ala
             20                  25                  30

Trp Met Asp Trp Val Arg Gln Ser Pro Glu Lys Gly Leu Glu Trp Val
         35                  40                  45

Ala Glu Ile Arg Ser Lys Ala Lys Asp His Ala Thr Tyr Tyr Ala Glu
     50                  55                  60

Ser Val Lys Gly Arg Phe Thr Ile Ser Arg Asp Asp Ser Lys Ser Ser
 65                  70                  75                  80

Val Tyr Leu Gln Met Asn Ser Leu Arg Ala Glu Asp Thr Gly Ile Tyr
                 85                  90                  95

Tyr Cys Thr Arg Gly Ser Ser Arg Trp Gly Gln Gly Thr Ser Val Thr
            100                 105                 110

Val Ser Ser Ala Gly Gly Gly Gly Ser Gly Gly Gly Gly Ser Gly Gly
        115                 120                 125

Gly Gly Ser Asp Ile Val Leu Thr Gln Ser Pro Ala Ser Leu Ala Val
    130                 135                 140

Ser Leu Gly Gln Arg Ala Thr Ile Ser Cys Arg Ala Ser Gln Ser Val
145                 150                 155                 160

Ser Thr Ser Thr Tyr Ser Tyr Met His Trp Tyr Gln Gln Lys Pro Gly
                165                 170                 175

Gln Pro Pro Lys Leu Leu Ile Tyr Ala Ser Asn Leu Glu Ser Gly
            180                 185                 190
```

```
Val Pro Ala Arg Phe Ser Gly Ser Gly Ser Gly Thr Asp Phe Thr Leu
        195                 200                 205

Asn Ile His Pro Val Glu Glu Glu Asp Thr Ala Thr Tyr Tyr Cys Gln
        210                 215                 220

Gln Ala Trp Glu Ile Pro Trp Thr Phe Gly Gly Gly Thr Thr Leu Glu
225                 230                 235                 240

Ile Arg Arg

<210> SEQ ID NO 13
<211> LENGTH: 744
<212> TYPE: DNA
<213> ORGANISM: homo sapiens

<400> SEQUENCE: 13
caggtccagc ttcagcagtc tggggctgaa ctggcaaaac ctggggcctc agtgaagatg     60
tcctgcaagg cttctggcta cacctttact agctactgga tgcactggat aaaacagagg    120
cctggacagg gtctggaatg gattggatac attaatccta gcactggtta tactgagtac    180
aatcagaagt tcaaggacaa ggccacattg actgcagaca atcctccag cacagcctac     240 atgcaactga gcagcctgac atctgaggac tctgcagtct attactgtgc aagggactac    300
tatgattacg aagatgttat ggactactgg ggtcaaggaa cctcagtcaa cgtctcctca    360
gccggtggag gcggttcagg cggaggtggc tctggcggtg cggatcgga cattgtgctg     420 acccaatctc cagcttcttt ggctgtgtct ctagggcaga gggccaccat ctcctgcaga    480
gccagcgaaa gtgttgatgg ttttggcatt agttttatga actggttcca acagaaacca    540
ggacagccac ccaaactcct catctatgct gcatccaacc aaggatccgg ggtccctgcc    600
aggtttagtg gcagtgggtc tgggacagac ttcagcctca acatccatcc tatggaggag    660
ggtgatgctg caatgtattt ctgtcagcaa attaaggagg ttccgtggac gttcggtgga    720
ggcaccaagc tggaaatcaa acgg                                           744

<210> SEQ ID NO 14
<211> LENGTH: 248
<212> TYPE: PRT
<213> ORGANISM: homo sapiens

<400> SEQUENCE: 14

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Trp Met His Trp Ile Lys Gln Arg Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Tyr Tyr Asp Tyr Glu Asp Val Met Asp Tyr Trp Gly Gln
            100                 105                 110

Gly Thr Ser Val Asn Val Ser Ser Ala Gly Gly Gly Ser Gly Gly
        115                 120                 125

Gly Gly Ser Gly Gly Gly Ser Asp Ile Val Leu Thr Gln Ser Pro
    130                 135                 140
```

```
Ala Ser Leu Ala Val Ser Leu Gly Gln Arg Ala Thr Ile Ser Cys Arg
145                 150                 155                 160

Ala Ser Glu Ser Val Asp Gly Phe Gly Ile Ser Phe Met Asn Trp Phe
                165                 170                 175

Gln Gln Lys Pro Gly Gln Pro Pro Lys Leu Leu Ile Tyr Ala Ala Ser
            180                 185                 190

Asn Gln Gly Ser Gly Val Pro Ala Arg Phe Ser Gly Ser Gly Ser Gly
        195                 200                 205

Thr Asp Phe Ser Leu Asn Ile His Pro Met Glu Glu Gly Asp Ala Ala
    210                 215                 220

Met Tyr Phe Cys Gln Gln Ile Lys Glu Val Pro Trp Thr Phe Gly Gly
225                 230                 235                 240

Gly Thr Lys Leu Glu Ile Lys Arg
                245
```

<210> SEQ ID NO 15
<211> LENGTH: 732
<212> TYPE: DNA
<213> ORGANISM: homo sapiens

<400> SEQUENCE: 15

```
gatgtgcagc tggtggagtc tgggggaggc ttagtgcagc ctggagggtc ccggaaactc     60
tcctgtgcag cctctggatt cactttcagt agctttggaa tgcactgggt tcgtcaggct    120
ccagagaagg ggctggagtg gtcgcatac attggtagtg gcagtagtac cgtctactat    180
gcagacacag tgaagggccg attcaccatc tccagagaca atcccaagaa caccctgttc    240
ctgcaaatga ccagtctaag gtctgaggac acggccatgt attactgtgc aagatcagag    300
acagctcggg ctgaggctat ggactactgg ggtcaaggaa cctcagtcac cgtctcctca    360
gccggtggag gcggttcagg cggaggtggc tctggcggtg gcggatcgga catccagatg    420
actcagtctc cagcctccct atctgcatct gtgggagaaa ctgtcaccat cacatgtcga    480
gcaagtggga atattcacaa ttatttagca tggtatcagc agaaacaggg aaaatctcct    540
cagctcctgg tctataatgc aaaaacctta gcagatggtg tgccatcaag gttcagtggc    600
agtggatcag gaacacaata ttctctcaag atcaacagcc tgcagcctga agattttggg    660
agttattact gtcaactttt ttggagtatt ccgtggacgt tcggtggagg caccaagctg    720
gaaaacaaac gg                                                        732
```

<210> SEQ ID NO 16
<211> LENGTH: 244
<212> TYPE: PRT
<213> ORGANISM: homo sapiens

<400> SEQUENCE: 16

```
Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Gly Ser Gly Ser Ser Thr Val Tyr Tyr Ala Asp Thr Val
    50                  55                  60

Lys Gly Arg Phe Thr Ile Ser Arg Asp Asn Pro Lys Asn Thr Leu Phe
65                  70                  75                  80
```

-continued

```
Leu Gln Met Thr Ser Leu Arg Ser Glu Asp Thr Ala Met Tyr Tyr Cys
                85                  90                  95

Ala Arg Ser Glu Thr Ala Arg Ala Glu Ala Met Asp Tyr Trp Gly Gln
            100                 105                 110

Gly Thr Ser Val Thr Val Ser Ser Ala Gly Gly Gly Gly Ser Gly Gly
        115                 120                 125

Gly Gly Ser Gly Gly Gly Gly Ser Asp Ile Gln Met Thr Gln Ser Pro
    130                 135                 140

Ala Ser Leu Ser Ala Ser Val Gly Glu Thr Val Thr Ile Thr Cys Arg
145                 150                 155                 160

Ala Ser Gly Asn Ile His Asn Tyr Leu Ala Trp Tyr Gln Gln Lys Gln
                165                 170                 175
Gly Lys Ser Pro Gln Leu Leu Val Tyr Asn Ala Lys Thr Leu Ala Asp
            180                 185                 190
Gly Val Pro Ser Arg Phe Ser Gly Ser Gly Ser Gly Thr Gln Tyr Ser
        195                 200                 205
Leu Lys Ile Asn Ser Leu Gln Pro Glu Asp Phe Gly Ser Tyr Tyr Cys
    210                 215                 220
Gln Leu Phe Trp Ser Ile Pro Trp Thr Phe Gly Gly Gly Thr Lys Leu
225                 230                 235                 240
Glu Asn Lys Arg

<210> SEQ ID NO 17
<211> LENGTH: 6
<212> TYPE: PRT
<213> ORGANISM: homo sapiens

<400> SEQUENCE: 17

Glu Pro Lys Ser Cys Asp
 1               5
```

US 7,083,950 B2

HIGH AFFINITY FUSION PROTEINS AND THERAPEUTIC AND DIAGNOSTIC METHODS FOR USE

This application is a continuation-in-part of U.S. application Ser. No. 09/787,835, filed Mar. 22, 2001, now abandoned, which is a National Stage of International Application No. PCT/US99/22045, filed Sep. 22, 1999, which is a continuation in part of U.S. application Ser. No. 09/313,942, filed May 19, 1999, now U.S. Pat. No. 6,472,179, which claims the benefit under 35 USC § 119(e) of U.S. Provisional Application No. 60/101,858, filed Sep. 25, 1998. The disclosures of these publications in their entireties are hereby specifically incorporated by reference into this application.

FIELD OF THE INVENTION

This invention relates to multimeric fusion proteins (designated herein as "trapbodies") with increased affinity for soluble, interacting proteins ("SIPs"), methods of producing such trapbodies, and methods for treating, diagnosing, or monitoring diseases or conditions in which regulation of SIP molecules is desired.

DESCRIPTION OF RELATED ART

Applicants have previously described the production of multimeric proteins that efficiently bind cytokines as set forth in U.S. Pat. No. 6,472,179 which is incorporated herein in its entirety. The use of cytokine receptor components to prepare fusion proteins that bind cytokines has also been described in PCT International Applications WO 96/11213 and WO 93/10151.

BRIEF SUMMARY OF THE INVENTION

The present invention provides trapbodies capable of binding soluble, interacting proteins ("SIPs") and preventing or inhibiting the SIPs from interacting with SIP targets. The trapbodies are useful for reducing, preventing, ameliorating or inhibiting conditions or diseases caused by normal or elevated levels of SIP molecules. The trapbodies of the invention are further useful in a variety of in vitro and in vivo diagnostic and prognostic assays.

Accordingly, in a first aspect, the invention features a SIP-specific fusion polypeptide comprising (i) one or more components which comprise a SIP binding domain of a SIP target ("target binding domain or TBD"); (ii) one or more components which comprise a SIP binding domain of an immunoglobulin ("immunoglobulin binding domain or IBD") and (iii) a multimerizing component, wherein the multimerizing component multimerizes with a multimerizing component on another SIP-specific fusion polypeptide to form a multimer of the SIP-specific fusion polypeptides. The multimer of the SIP-specific fusion polypeptides is termed a "trapbody" and is capable of binding to a SIP. In this aspect of the invention, the one or more SIP binding domain(s) of an immunoglobulin is (are) immuno-specific for the same SIP which binds the SIP target binding domain of (i). In preferred embodiments, they are immunospecific for different epitopes of the SIP molecule.

In one embodiment, the SIP is a cytokine, and the SIP target is a cytokine receptor. In one aspect of this embodiment, the SIP target binding domain(s) is (are) derived from the specificity-determining component of a cytokine receptor protein or a cytokine binding fragment or derivative thereof. As used herein, a specificity-determining component of a receptor is one that specifically binds a cytokine, leading to its interaction with a second receptor component which is a signaling receptor component. The specificity-determining components of cytokine receptors that are useful for practicing this invention, include, but are not limited to, those set forth in U.S. Pat. No. 6,472,179. These include the specificity-determining components of receptors for interleukin-1 (IL-1), IL-2, IL-3, IL-4, IL-5, IL-6, IL-7, IL-9, IL-10, IL-11, IL-13, IL-15, IL-18, granulocyte macrophage colony stimulating factor, oncostatin M, leukemia inhibitory factor, ciliary neurotrophic factor, interferon-gamma, and cardiotrophin-1. In an embodiment wherein the SIP is IL-1, the specificity-determining component is a specificity-determining component of the IL-1 receptor or a fragment or derivative thereof. In a more specific embodiment, the IL-1 receptor protein is the cytokine binding portion of the IL-1R1 Type I or Type II protein. In another embodiment, the target molecule is IL-4, and the cytokine receptor protein is human IL-4Rα, or a fragment or derivative thereof.

In a related embodiment, the SIP target-binding domain is derived from a signaling component of a cytokine receptor or a cytokine binding fragment or derivative thereof. As used herein, a signaling component is defined as a receptor component that initiates cell signaling upon the interaction with another cytokine receptor component, which can be either a specificity-determining component or another signaling component of the cytokine receptor. A cytokine binding fragment or derivative of a signaling component is one that binds the cytokine alone or in the presence of a specificity-determining component of the receptor system. The signaling components of cytokine receptors that are useful for practicing this invention, include, but are not limited to, those set forth in U.S. Pat. No. 6,472,179. These include the signaling components of receptors for IL-1, IL-2, IL-3, IL-4, IL-5, IL-6, IL-7, IL-9, IL-10, IL-11, IL-13, IL-15, IL-18, granulocyte macrophage colony stimulating factor, oncostatin M, leukemia inhibitory factor, ciliary neurotrophic factor, MIF, interferon gamma and cardiotrophin-1. In one embodiment wherein the SIP is IL-1, the signaling component is a signaling component of the IL-1 receptor system, such as IL-1R accessory protein. In yet another embodiment, wherein the SIP is IL-4, the signaling component is IL-2Rγ.

In a second aspect, the invention provides a SIP-specific fusion polypeptide comprising (i) two or more components which comprise a SIP binding domain of an immunoglobulin and (ii) a multimerizing component, wherein the multimerizing component multimerizes with a multimerizing component on another SIP-specific fusion polypeptide to form a trapbody capable of binding to a SIP. In this aspect of the invention, the two or more SIP binding domains of an immunoglobulin are immuno-specific for the same or different epitopes of the same SIP.

In one embodiment, the components of the SIP-specific fusion polypeptides of the invention are connected directly to each other. In other embodiments, a spacer sequence may be included between one or more components, which may comprise one or more molecules, such as amino acids. For example, a spacer sequence may include one or more amino acids naturally connected to a domain-containing component. A spacer sequence may also include a sequence used to enhance expression of the fusion protein, provide restriction sites, allow component domains to form optimal tertiary or quaternary structures and/or to enhance the interaction of a component with its SIP. In one embodiment, the SIP-specific fusion polypeptide of the invention comprises one or more peptide sequences between one or more components which is (are) between 1 and 100 amino acids. In a preferred embodiment, the peptide sequence is between 1 and 25 amino acids.

Further embodiments may include a signal sequence at the beginning or amino-terminus of a SIP-specific fusion polypeptide of the invention. Such a signal sequence may be native to the cell, recombinant, or synthetic.

The components of the SIP-specific fusion polypeptide of the invention may be arranged in a variety of configurations. For example, in certain embodiments, described from the beginning or amino-terminus of the fusion protein, one or more components comprising SIP target binding domain(s) (TBD) may be followed by one or more components comprising SIP-directed immunoglobulin binding domains (IBD), followed by a multimerizing component (M). Such a fusion protein may also optionally include a signal sequence (SS) prior to the one or more TBD or IBD(s).

Further configurations contemplated by the invention may be depicted as follows:

$(TBD)_x$-$(IBD)_y$-M;
$(TBD)_x$-M-$(IBD)_y$;
$(IBD)_x$-$(TBD)_y$-M;
SS-$(TBD)_x$-$(IBD)_y$-M;
SS-$(IBD)_x$-$(TBD)_y$-M;
$(IBD)_x$-M-$(IBD)_y$;
SS-$(IBD)_x$-M-$(IBD)_y$;
$(IBD)_x$-$(IBD)_y$-M;
SS-$(IBD)_x$-$(IBD)_y$-M;

wherein $x \geqq 1$ and $y \geqq 1$. In each embodiment, the one or more IBDs or TBDs may be directed to the same or different epitopes of the receptor. In one specific embodiment, x=1–10 and y=1–10. In an even more specific embodiment, x=1 and y=1, or x=2 and y=2. In a preferred embodiment, the fusion polypeptide has the arrangement $(IBD)_x$-$(IBD)_y$-M, wherein the first and second IBD domains are immuinospecific for different epitopes of the SIP, and x=1 and y=1. In another preferred embodiment, the fusion polypeptide has the arrangement $(IBD)_x$-$(TBD)_y$-M wherein x=1 and y=1.

In a third aspect, the invention features a trapbody comprising a dimer of two SIP-specific fusion polypeptides, wherein each polypeptide consists of (i) one or more components which comprise a SIP binding domain of a SIP target; (ii) one or more components which comprise a SIP binding domain of an immunoglobulin and (iii) a multimerizing component.

In a fourth aspect, the invention features a trapbody comprising a dimer of two SIP-specific fusion polypeptides, wherein each polypeptide consists of (i) two or more components which comprise a SIP binding domain of an immunoglobulin and (ii) a multimerizing component.

In a fifth aspect, the invention features a nucleic acid sequence encoding a SIP-specific fusion polypeptide which comprises (i) one or more components which comprise a SIP binding domain of a SIP target; (ii) one or more components which comprise a SIP binding domain of an immunoglobulin and (iii) a multimerizing component, wherein the multimerizing component multimerizes with a multimerizing component on another SIP-specific fusion polypeptide to form a multimer of the fusion polypeptides. In other embodiments, the nucleic acid encodes a SIP-specific fusion polypeptide comprising (i) two or more components which comprise a SIP binding domain of an immunoglobulin, and (ii) a multimerizing component.

In a related sixth aspect, the invention features a vector comprising a nucleic acid sequence of the invention. The invention further features an expression vector comprising a nucleic acid of the invention, wherein the nucleic acid molecule is operably linked to an expression control sequence. Also provided is a host-vector system for the production of the fusion polypeptides and trapbodies of the invention which comprises the expression vector of the invention which has been introduced into a host cell or organism, including, but not limited to, transgenic animals, suitable for expression of the fusion polypeptides and trapbodies. Suitable host cells include, for example, bacterial cells, e.g., *E. coli,* yeast cells, e.g., *Pichia pastoris,* insect cells, e.g., *Spodoptera frugiperda,* or mammalian cells, such as CHO or COS.

In a related seventh aspect, the invention features a method of producing a fusion polypeptide or trapbody of the invention, comprising culturing a host cell transfected with a vector comprising a nucleic acid sequence of the invention, under conditions suitable for expression of the protein from the host cell, and recovering the fusion protein or trapbody so produced.

In an eighth aspect, the invention features therapeutic methods for the treatment of a SIP-related disease or condition, comprising administering a therapeutically effective amount of a trapbody to a subject in need thereof, wherein the relevant SIP molecule is reduced or removed, and the SIP-related disease or condition is ameliorated or inhibited. In a related aspect, the trapbody of the invention may be used in conjunction with the therapeutic use of the SIP to control and/or monitor its levels.

Accordingly, in a ninth aspect, the invention features pharmaceutical compositions comprising a trapbody of the invention with a pharmaceutically acceptable carrier. Such pharmaceutical compositions may comprise trapbodies or nucleic acids which encode them.

In a tenth aspect, the invention features diagnostic and prognostic methods, as well as kits, for detecting, quantitating, and/or monitoring target molecule levels using a trapbody of the invention.

Other objects and advantages will become apparent from a review of the ensuing detailed description.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, references to "a method" include one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to describe the methods and/or materials in connection with which the publications are cited.

General Description

The invention encompasses trapbodies capable of binding and inhibiting the activity of soluble, interacting proteins ("SIPs"). The trapbodies are multimers, preferably dimers, of SIP-specific fusion polypeptides which comprise SIP binding domains derived from SIP targets and/or anti-SIP immunoglobulins, as well as multimerizing components. Generally, the multimerizing component is any component capable of multimerizing, e.g., forming a higher order complex of two or more fusion proteins. In one embodiment, the SIP-specific fusion polypeptides which form the trapbody are comprised of (i) one or more components which comprise a SIP binding domain of a SIP target; (ii) one or more components which comprise a SIP binding domain of an anti-SIP immunoglobulin and (iii) a multimerizing component, wherein the multimerizing component multimerizes with a multimerizing component on another fusion polypeptide to form a multimer of the fusion polypeptides. In another embodiment, the fusion polypeptides which form the trapbody are comprised of (i) two or more components which comprise a SIP binding domain of an anti-SIP immunoglobulin and (ii) a multimerizing component, wherein the multimerizing component multimerizes with a multimerizing component on another fusion polypeptide to form a multimer of the fusion polypeptides.

Definitions

By the term "inhibitor" is meant a substance that retards or prevents either upregulation or downregulation of a biological response. By inhibiting a SIP that normally results in downregulation of a biological activity, the desired result is upregulation of such activity. Conversely, by inhibiting a SIP that normally results in upregulation of a biological activity, the desired result is downregulation of such activity. Common blockers or inhibitors include but are not limited to inhibitory ribozymes, siRNAs, aptamers, antisense molecules, antibodies, antagonists and their derivatives. More specifically, an example of an inhibitor of a cytokine is a cytokine trap, as described in parent application Ser. No. 09/313,942 which issued as U.S. Pat. No. 6,472,179.

By the term "soluble interacting protein (SIP)" is meant any protein that is secreted or is circulating and which binds a receptor target and acts as an agonist or an antagonist. SIPs include, but are not limited to, cytokines, hormones, and growth factors.

By the term "soluble interacting protein target (SIP target)" is meant any protein which, when bound by a SIP, is either agonized (activated) or antagonized (inactivated).

By the term "SIP binding domain of a SIP target or TBD" is meant the entire SIP target, including, but not limited to, full length receptors, as well as soluble (extracellular) domains thereof, as well as portions or functionally equivalent derivatives of such targets which bind to a SIP. This is intended to include not only the complete wild-type domain, but also insertional, deletional, and substitutional variants thereof which substantially retain the functional characteristics of the intact domain. It will be readily apparent to one of skill in the art that numerous variants of the above SIP target binding domain can be obtained which will retain substantially the same functional characteristics as the wild-type domain.

By the term "SIP binding domain of an immunoglobulin (immunoglobulin binding domain or IBD)" is meant that portion of an immunoglobulin that binds to a SIP, or functionally equivalent derivatives which bind an SIP. Thus, the term immunoglobulin binding domain, as used herein, includes full antibodies, as well as antibody fragments either produced by the modification of whole antibodies (e.g. enzymatic digestion), or those synthesized de novo using recombinant DNA methodologies (e.g., single chain Fv) (scFv)) or those identified using phase display libraries (see, for example, McCafferty et al. (1990) Nature 348:552–554). Immuglobulin binding domains also include, but are not limited to, the variable regions of the heavy ($V_H$) or the light ($V_L$) chains of immunoglobulins. Methods for producing such variable regions are described in Reiter, et al. (1999) J. Mol. Biol. 290:685–698. This is intended to include not only the wild-type domain, also insertional, deletional, and substitutional variants thereof which substantially retain the functional characteristics of the intact domain. It will be readily apparent to one of skill in the art that numerous variants of the immunoglobulin binding domain can be obtained which will retain substantially the same functional characteristics as the wild-type domain.

The term "functionally equivalent" when used in reference to an SBD oran IBD, is intended to encompass such a domain with at least one alteration, e.g., a deletion, addition, and/or substitution, which retains substantially the same functional characteristics as does the wild type SBD or IBD domain, that is, a substantially equivalent binding to a SIP. It will be appreciated that various amino acid substitutions can be made in an SBD or IBD without departing from the spirit of the invention with respect to the ability of these components to bind a SIP. The functional characteristics of the traps of the invention may be determined by any suitable screening assay known to the art for measuring the desired characteristic. Examples of such assays are described in the experimental section below which allow determination of the affinity of the traps for binding a SIP (Kd), as well as their half-life ($T_{1/2}$). Other assays, for example, a change in the ability to specifically bind to a SIP can be measured by a competition-type SIP binding assay. Modifications of protein properties such as thermal stability, hydrophobicity, susceptibility to proteolytic degradation, or tendency to aggregate may be measured by methods known to those of skill in the art.

By the term "multimerizing component" is meant a component which allows a single polypeptide to form a multimer with one or more other polypeptides. With respect to each multimerizing components described herein, the component may be the wild type sequence, or a functionally equivalent derivative thereof. Preferably, the multimeric protein is a dimer. In some embodiments, the multimerizing component comprises an immunoglobulin—derived domain from, for example, human IgG, IgM or IgA, or comparable immunoglobulin domains from other animals, including, but not limited to, mice. In specific embodiments, the immunoglobulin-derived domain may be selected from the group consisting of the Fc domain of IgG, the heavy chain of IgG, and the light chain of IgG. The Fc domain of IgG may be selected from the isotypes IgG1, IgG2, IgG3, and IgG4, as well as any allotype within each isotype group. In addition, the multimerizing component may be an Fc fragment or an amino acid sequence of 1 to about 200 amino acids in length containing at least one cysteine residue. In other embodiments, the multimerizing component is cysteine, or a short, cysteine-containing peptide. In addition, the multimerizing component may be unrelated to immunoglobulins and be, for example, a leucine zipper, a helix loop motif, or a coiled-coil motif. The embodiments in which the multimerizing component is smaller than the full length Fc component are termed "mini-trapbodies" and are particularly useful in specific applications where a smaller size allows the mini-trapbodies to penetrate to a target tissue.

The term "spacer" or "linker" means one or more molecules, e.g., nucleic acids or amino acids, or nonpeptide moieties, such as polyethylene glycol, which may be inserted between one or more component domains. For example, spacer sequences may be used to provide a restriction site between components for ease of manipulation. A spacer may also be provided to enhance expression of the fusion protein from a host cell, to decrease steric hindrance such that the component may assume its optimal tertiary or quaternary structure and/or interact appropriately with its target molecule. For spacers and methods of identifying desirable spacers, see, for example, George et al. (2003) Protein Engineering 15:871–879, herein specifically incorporated by reference. One example of a spacer is $(G_4S)_3$ (SEQ ID NO:2) encoded by the nucleotide sequence of SEQ ID NO: 1.

SIP Binding Immunoglobulins and Binding Domains

The SIP-specific fusion polypeptides and trapbodies of the invention comprise one or more immunoglobulin binding domains isolated from antibodies generated against a selected SIP. The term "immunoglobulin or antibody" as used herein refers to a mammalian, including human, polypeptide comprising a framework region from an immunoglobulin gene or fragments thereof that specifically binds and recognizes an antigen, which, in the case of the present invention, is a SIP or portion thereof. If the intended trapbody will be used as a mammalian therapeutic, immunoglobulin binding regions should be derived from the corresponding mammalian immunoglobulins. If the trapbody is intended for non-therapeutic use, such as for diagnostics and ELISAs, the immunoglobulin binding regions may be derived from either human or non-human mammals, such as mice. The human immunoglobulin genes or gene fragments include the kappa, lambda, alpha, gamma, delta, epsilon, and mu constant regions, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Within each IgG class, there are different isotypes (eg. $IgG_1$, $IgG_2$, etc.) as well as allotypes thereof. Typically, the antigen-binding region of an antibody will be the most critical in determining specificity and affinity of binding.

An exemplary immunoglobulin (antibody) structural unit of human IgG, comprises a tetramer. Each tetramer is composed of two identical pairs of polypeptide chains, each pair having one light chain (about 25 kD) and one heavy chain (about 50–70 kD). The N-terminus of each chain defines a variable region of about 100–110 or more amino acids primarily responsible for antigen recognition. The terms "variable light chain" ($V_L$) and variable heavy chain ($V_H$) refer to these light and heavy chains respectively.

Antibodies exist as intact immunoglobulins, or as a number of well-characterized fragments produced by digestion with various peptidases. For example, pepsin digests an antibody below the disulfide linkages in the hinge region to produce $F(ab)'_2$, a dimer of Fab which itself is a light chain joined to $V_H$-$C_H$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology. Thus, the terms antibody, as used herein, also includes antibody fragments either produced by the modification of whole antibodies, or those synthesized de novo using recombinant DNA methodologies (e.g., single chain Fv)(scFv)) or those identified using phage display libraries (see, for example, McCafferty et al. (1990) Nature 348:552–554). In addition, the SIP binding component of the fusion polypeptides and trapbodies of the invention include the variable regions of the heavy ($V_H$) or the light ($V_L$) chains of immunoglobulins, as well as SIP binding portions thereof. Methods for producing such variable regions are described in Reiter, et al. (1999) J. Mol. Biol. 290:685–698.

Methods for preparing antibodies are known to the art. See, for example, Kohler & Milstein (1975) Nature 256: 495–497; Harlow & Lane (1988) *Antibodies: a Laboratory Manual*, Cold Spring Harbor Lab., Cold Spring Harbor, N.Y.). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity. Techniques for the production of single chain antibodies or recombinant antibodies (U.S. Pat. Nos. 4,946,778; 4,816,567) can be adapted to produce antibodies used in the fusion proteins and methods of the instant invention. Also, transgenic mice, or other organisms such as other mammals, may be used to express human or humanized antibodies. Alternatively, phage display technology can be used to identify antibodies, antibody fragments, such as variable domains, and heteromeric Fab fragments that specifically bind to selected antigens. Phage display is of particular value to isolate weakly binding antibodies or fragments thereof from unimmunized animals which, when combined with other weak binders in accordance with the invention described herein, create strongly binding trapbodies.

Screening and selection of preferred immunoglobulins (antibodies) can be conducted by a variety of methods known to the art. Initial screening for the presence of monoclonal antibodies specific to a SIP may be conducted through the use of ELISA-based methods or phage display, for example. A secondary screen is preferably conducted to identify and select a desired monoclonal antibody for use in construction of the trapbodies of the invention. Secondary screening may be conducted with any suitable method known to the art. One preferred method, termed "Biosensor Modification-Assisted Profiling" ("BiaMAP") is described in co-pending U.S. Ser. No. 60/423,017 filed 01 Nov. 2002, herein specifically incorporated by reference in its entirety. BiaMAP allows rapid identification of hybridoma clones producing monoclonal antibodies with desired characteristics. More specifically, monoclonal antibodies are sorted into distinct epitope-related groups based on evaluation of antibody: antigen interactions.

Nucleic Acid Construction and Expression

Individual components, SIP-specific fusion proteins, and the trapbodies of the invention may be produced from nucleic acids molecules using molecular biological methods known to the art. When the nucleic acids encode fusion polypeptides which comprise (i) one or more components which comprise a SIP binding domain of a SIP target; (ii)

one or more components which comprise a SIP binding domain of an immunoglobulin and (iii) a multimerizing component, the multimerizing component multimerizes with a multimerizing component on another fusion polypeptide to form a trapbody or mini-trapbody of the invention. In other embodiments, the nucleic acid encodes fusion polypeptides comprising (i) two or more components which comprise a SIP binding domain of an immunoglobulin, and (ii) a multimerizing component, and the encoded polypeptides multimerize to form the trapbodies and mini-trapbodies of the invention. Nucleic acid molecules are inserted into a vector that is able to express the fusion proteins when introduced into an appropriate host cell. Appropriate host cells include, but are not limited to, bacterial, yeast, insect, and mammalian cells. Any of the methods known to one skilled in the art for the insertion of DNA fragments into a vector may be used to construct expression vectors encoding the fusion proteins of the invention under control of transcriptional/translational control signals. These methods may include in vitro recombinant DNA and synthetic techniques and in vivo recombinations (See Sambrook et al. *Molecular Cloning, A Laboratory Manual,* Cold Spring Harbor Laboratory; Current Protocols in Molecular Biology, Eds. Ausubel, et al., Greene Publ. Assoc., Wiley-Interscience, NY).

Expression of the nucleic acid molecules of the invention may be regulated by a second nucleic acid sequence so that the molecule is expressed in a host transformed with the recombinant DNA molecule. For example, expression of the nucleic acid molecules of the invention may be controlled by any promoter/enhancer element known in the art. Promoters which may be used to control expression of the fusion polypeptide molecules include, but are not limited to, the long terminal repeat as described in Squinto et al. (1991) Cell 65:1–20; the SV40 early promoter region, the CMV promoter, the M-MuLV 5' terminal repeat the promoter contained in the 3' long terminal repeat of Rous sarcoma virus, the herpes thymidine kinase promoter, the regulatory sequences of the metallothionine gene; prokaryotic expression vectors such as the β-lactamase promoter, or the tac promoter (see also "Useful proteins from recombinant bacteria" in Scientific American (1980) 242:74–94); promoter elements from yeast or fungi such as the Gal 4 promoter, the ADH (alcohol dehydrogenase) promoter, PGK (phosphoglycerol kinase) promoter, alkaline phosphatase promoter, and tissue-specific transcriptional control regions derived from elastase I gene, insulin gene, immunoglobulin gene, mouse mammary tumor virus, albumin gene, α-fetoprotein gene, α1-antitrypsin gene, β-globin gene, myelin basic protein gene, myosin light chain-2 gene, and gonadotropic releasing hormone gene.

$V_L$ and $V_H$ domains. In accordance with the invention, the nucleic acid constructs include regions which encode SIP binding domains of immunoglobulins. In general, such binding domains will be derived from heavy ($V_H$) or light ($V_L$) chain variable regions. After identification and selection of antibodies exhibiting desired binding characteristics, the variable regions of the heavy chains and/or light chains of each antibody is isolated, amplified, cloned and sequenced. Modifications may be made to the $V_H$ and $V_L$ nucleotide sequences, including additions of nucleotide sequences encoding amino acids and/or carrying restriction sites, deletions of nucleotide sequences encoding amino acids, or substitutions of nucleotide sequences encoding amino acids.

SIP target-binding domains. In accordance with the invention, the nucleic acid constructs include components which encode SIP target-derived binding domains. In preferred embodiments, such targets are SIP receptors. After identification of SIP binding domains exhibiting desired binding characteristics, the nucleic acids that encode such domains are used in the nucleic acid constructs. Such nucleic acids may be modified, including additions of nucleotide sequences encoding amino acids and/or carrying restriction sites, deletions of nucleotide sequences encoding amino acids, or substitutions of nucleotide sequences encoding amino acids.

The nucleic acid constructs of the invention are inserted into an expression vector or viral vector by methods known to the art, wherein the nucleic acid molecule is operatively linked to an expression control sequence. Also provided is a host-vector system for the production of a trapbody of the invention, which comprises the expression vector of the invention, which has been introduced into a host cell suitable for expression of the trapbody. The suitable host cell may be a bacterial cell such as *E. coli*, a yeast cell, such as *Pichia pastoris,* an insect cell, such as *Spodoptera frugiperda,* or a mammalian cell, such as a COS, CHO, 293, BHK or NS0 cell.

The invention further encompasses methods for producing the trapbodies of the invention by growing cells transformed with an expression vector under conditions permitting production of the SIP-specific fusion polypeptides and recovery of the trapbodies so produced. Cells may also be transduced with a recombinant virus comprising the nucleic acid construct of the invention.

The trapbodies may be purified by any technique, which allows for the subsequent formation of a stable SIP-specific protein. For example, and not by way of limitation, the trapbodies may be recovered from cells either as soluble proteins or as inclusion bodies, from which they may be extracted quantitatively by 8M guanidinium hydrochloride and dialysis. In order to further purify the trapbodies, conventional ion exchange chromatography, hydrophobic interaction chromatography, reverse phase chromatography or gel filtration may be used. The trapbodies may also be recovered from conditioned media following secretion from eukaryotic or prokaryotic cells.

Diagnostic Methods

The compositions of the instant invention may be used diagnostically as well as prognostically. For example, a trapbody of the invention may be used to detect the presence of a particular SIP in a biological sample in order to quantitate the SIP levels or to determine if a subject has elevated SIP levels. Further, a trapbody of the invention can be used to monitor levels of SIPs in a biological sample obtained from a subject. The trapbodies of the invention can be used in methods known in the art relating to the localization and activity of SIPs.

Screening and Detection Methods

The trapbodies of the invention may also be used in in vitro or in vivo screening methods where it is desirable to detect and/or measure SIP levels. Screening methods are well known to the art and include cell-free, cell-based, and animal assays. In vitro assays can be either solid state or soluble. SIP detection may be achieved in a number of ways known to the art, including the use of a label or detectable group capable of identifying a trapbody, which has trapped or otherwise bound a SIP. Detectable labels are well developed in the field of immunoassays and may generally be used in conjunction with assays using the trapbody of the invention.

The trapbodies of the invention may also be directly or indirectly coupled to a label or detectable group when desirable for the purpose it is being used. A wide variety of labels may be used, depending on the sensitivity required, ease of conjugation, stability requirements, available instrumentation, and disposal provisions.

Therapeutic Methods

The trapbodies of the invention can be used to ameliorate any disease or condition resulting from the action of one or more SIP molecules ("SIP-related condition or disease."). These generally encompass diseases or conditions of a mammalian host, particularly a human host, which are associated with, or caused by, a particular SIP molecule. Thus, treating a SIP-related condition or disease will encompass the treatment of a mammal, in particular, human, who has symptoms reflective of increased SIP levels, or who is expected to have such elevated SIP levels in response to a disease, condition or treatment regimen. Treating a SIP-related condition or disease encompasses the use of a trapbody or trapbody-encoding nucleic acid of the invention to ameliorate an undesirable symptom resulting from the SIP-related condition or disease. The trapbodies of the invention trap and inactivate the SIP molecule such that the SIP is prevented from attaching to SIP targets naturally circulating or present on cells in the subject being treated. In some circumstances, the trapbody accelerates clearance of the SIP from the circulation. Accordingly, administration of the trapbody of the invention to a subject suffering from a disease or condition associated with the activity or presence of a SIP results in amelioration or inhibition of the disease or condition. Further, the trapbody of the invention can be used prophylactically, both systemically and locally, to prevent an undesirable symptom or disease or condition from occurring or developing in a subject at risk for the development of the undesirable symptom, disease or condition. As used herein, a SIP-related condition also includes a condition in which it is desirable to alter, either transiently, or long-term, levels of a particular SIP in order to steer an immune response. SIP-related conditions also include those in which SIPs are administered therapeutically, wherein the trapbody of the invention is utilized to control SIP levels.

In a preferred embodiment of the present invention, the SIP is a cytokine. Pro-inflammatory cytokines such as IL-1 and TNF have been implicated in a variety of diseases including renal injury and rheumatoid arthritis (see, for example, Arend (2001) Semin. Arthritis. Rheum. 30:1–6). Elevated serum IL-8 levels are associated with disease activity in idiopathic intermediate uveitis (Klok et al. (1998) Br. J. Ophthalmol. 82:871–874. Elevated IL-4, IL-5, IL-6, and IL-13 are associated with chronic inflammatory airway diseases (Hamelmann et al. (2001) Immunol. Rev. 179: 182–191). Excessive secretion of cytokines such as IFN-γ, IL-1, IL-12, IL-6, IL-18, and TNF-α are present in inflammatory bowel diseases such as Crohn—s disease and ulcerative colitis (Hoang et al. (1994) Acta Gasatroenterol. Belg. 57:219–223). Over-expression of IL-6 is implicated in the pathology of a number of diseases, such as multiple myeloma, rheumatoid arthritis, Castleman's disease, psoriasis, and osteoporosis (Simpson et al. (1997) Protein Science 6:929–955). IL-1, TNF-α, and INF-γ have been implicated in periodontal diseases (Alexander et al. (1994) Curr. Opin. Periodontol Jan:39–53).

IL-18 is elevated in synovial fluid from patients suffering from rheumatoid arthritis (Gracie et al. (1999) J. Clin. Invest.104:1393–1401). In a mouse arthritis model, neutralization of IL-18 resulted in a therapeutic effect (Plater-Zyberk (2001) J. Clin. Invest. 108:1825–1832). The expression of IL-18 and IL-18 receptor on various cell types in human atherosclerotic lesions has recently been described (Gerdes et al. (2002) J. Exp. Med. 195:245–257). Blockade of IL-18 reduced formation of new lesions and resulted in improvement of established lesions (Mallat et al. (2001) Circ. Res. 89:E41–45). These data have implicated IL-18 as playing an important role in the proinflammatory component of artherosclerosis.

In the treatment of a particular disease or condition associated with increased levels of one or more SIPs, the trapbodies of the invention may be administered alone or in combination to effectively lower the level of the SIP(s).

Methods of Administration

Methods known in the art for the therapeutic delivery of agents such as proteins or nucleic acids can be used for the therapeutic delivery of a trapbody or a nucleic acid encoding a trapbody of the invention for reducing SIP levels in a subject, e.g., cellular transfection, gene therapy, direct administration with a delivery vehicle or pharmaceutically acceptable carrier, indirect delivery by providing recombinant cells comprising a nucleic acid encoding a trapbody of the invention.

Various delivery systems are known and can be used to administer the trapbody of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429–4432), construction of a nucleic acid as part of a retroviral or other vector, etc. Methods of introduction can be enteral or parenteral and include but are not limited to intradermal, intramuscular, intraperitoneal, intravenous, subcutaneous, pulmonary, intranasal, intraocular, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, said implant being of a porous, non-porous, or gelatinous material, including membranes, such as sialastic membranes, fibers, or commercial skin substitutes.

In another embodiment, the active agent can be delivered in a vesicle, in particular a liposome (see Langer (1990) Science 249:1527–1533). In yet another embodiment, the active agent can be delivered in a controlled release system. In one embodiment, a pump may be used (see Langer (1990) supra). In another embodiment, polymeric materials can be used (see Howard et al. (1989) J. Neurosurg. 71:105). In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864–1868), etc. Alternatively, a nucleic acid can be introduced intracellularly and incorporated within host cell DNA for expression, by homologous recombination.

Cellular Transfection and Gene Therapy

The present invention encompasses the use of nucleic acids encoding the fusion polypeptides and trapbodies of the invention for transfection of cells in vitro and in vivo. These nucleic acids can be inserted into any of a number of well-known vectors for transfection of target cells and organisms. The nucleic acids are transfected into cells ex vivo and in vivo, through the interaction of the vector and the target cell. The compositions are administered (e.g., by injection into a muscle) to a subject in an amount sufficient to elicit a therapeutic response. An amount adequate to accomplish this is defined as "a therapeutically effective dose or amount."

In another aspect, the invention provides a method of reducing SIP levels in a human or other animal comprising transfecting a cell with a nucleic acid encoding a fusion polypeptide or trapbody of the invention, wherein the nucleic acid comprises an inducible promoter operably linked to the nucleic acid encoding the fusion polypeptide or trapbody. For gene therapy procedures in the treatment or prevention of human disease, see for example, Van Brunt (1998) Biotechnology 6:1149–1154.

Combination Therapies

In numerous embodiments, the trapbodies of the present invention may be administered in combination with one or more additional compounds or therapies. For example, multiple trapbodies can be co-administered, or one or more trapbodies can be administered in conjunction with one or more therapeutic compounds. The combination therapy may encompass simultaneous or alternating administration. In addition, the combination may encompass acute or chronic administration.

Pharmaceutical Compositions

The present invention also provides pharmaceutical compositions comprising a fusion protein or trapbody of the invention and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

In a preferred embodiment, the composition is formulated in accordance with routine procedures as a pharmaceutical composition adapted for intravenous administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The active agents of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the trapbody of the invention which will be effective in the treatment of a SIP-related condition or disease can be determined by standard clinical techniques based on the present description. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Kits

The invention also provides a pharmaceutical pack or kit comprising one or more containers filled with at least one trapbody of the invention. The kits of the invention may be used in any applicable method, including, for example, diagnostically. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Transgenic Animals

The invention includes transgenic non-human animals expressing a trapbody protein of the invention. A transgenic animal can be produced by introducing nucleic acid into the male pronuclei of a fertilized oocyte, e.g., by microinjection, retroviral infection, and allowing the oocyte to develop in a pseudopregnant female foster animal. Any of the regulatory or other sequences useful in expression vectors can form part of the transgenic sequence. A tissue-specific regulatory sequence(s) can be operably linked to the transgene to direct expression of the transgene to particular cells. A transgenic non-human animal expressing a fusion polypeptide or trapbody of the invention is useful in a variety of applications, including as a means of producing such a fusion proteins Further, the transgene may be placed under the control of an inducible promoter such that expression of the fusion polypeptide or trapbody may be controlled by, i.e., administration of a small molecule.

Specific Embodiments

Example 1 illustrates one embodiment of the trapbodies of the invention, wherein the SIP is the cytokine IL-18. The trapbody is composed of different arrangements of a binding domain of the IL-18 receptor and/or an anti-IL-18 immunoglobulin-derived binding region, each with a multimerizing component. More specifically, fusion proteins were constructed with an IL-18 receptor component alpha (IL-18Rα) (SEQ ID NO:3), an anti-IL-18 scFv (SEQ ID NO:5), and a multimerizing component (Fc). Affinity determinations (Table 1) demonstrate that the combination of the specificity determining component of a cytokine receptor and a specific anti-cytokine antibody results in a molecule that has increased affinity for the cytokine over each component separately. Thus, they provide support for the use of the cytokine-specific fusion proteins of the present invention to reduce cytokine levels in diseases or conditions in which such cytokine levels are elevated.

Example 2 illustrates one embodiment of the trapbodies of the invention composed of anti-cytokine scFv components to the same or different epitopes on the cytokine, each connected to a multimerizing (Fc) component. As shown in Table 2, the bispecific scFv-scFv-Fc fusion proteins tested exhibited increased affinity for hIL-6 over that of the monospecific fusion proteins. The range of increased affinity is from ~6 fold to 200-fold.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

IL-18 Traps: Receptor-ScFv Fusion Proteins

Construction of Receptor-ScFv-Fc fusions. DNA constructs encoding the following orientations of cytokine receptor-scFv-Fc fusions were made:
(1) the extracellular domain of human IL-18 receptor alpha (hIL-18Rα) (SEQ ID NO:4)-($G_4S$)$_3$ (SEQ ID NO:2)-anti-human IL-18 single chain Fv (anti-hIL-18 scFv) (SEQ ID NO:6)-Fc domain of human IgG1 (Fc) (SEQ ID NO:7);
(2) anti-hIL-18 scFv (SEQ ID NO:6)-($G_4S$)$_3$ (SEQ ID NO:2)-hIL-18Rα (SEQ ID NO:4)-Fc (SEQ ID NO:7);
(3) hIL-18Rα (SEQ ID NO:3)-Fc (SEQ ID NO:7)-anti-hIL-18 scFv (SEQ ID NO:6);
(4) anti-hIL-18 scFv (SEQ ID NO:6)-Fc (SEQ ID NO:7)-hIL-18Rα (SEQ ID NO:3);
(5) hIL-18Rα (SEQ ID NO:3)-Fc (SEQ ID NO:7) and
(6) anti-hIL-18 scFv (SEQ ID NO:6)-Fc.

The extracellular domain, nucleotides 76–1011 (amino acids 18–329) (SEQ ID NO:3) of human IL-18 Receptor α (Genbank #U43672) was PCR cloned from spleen cDNA. The anti-human IL-18 ScFv was constructed by overlapping oligonucleotide synthesis and PCR that resulted in fusing the heavy chain variable region (nucleotides 58 to 396; amino acids 20–132, Genbank #AB017433) to a nucleotide sequence (SEQ ID NO:1) encoding the amino acid sequence, ($G_4S$)$_3$ (SEQ ID NO:2), fused to the light chain variable region (nucleotides 61–384 (amino acids 21–128; Genbank Accession #AB017434) ($V_H$-$V_L$) (SEQ ID NO:5). The Fc domain of human IgG1 comprises nucleotides 79–765 (amino acids 27–255) of the human IgG1 Fc domain (Genbank #X70421), containing a nucleotide change at nucleotide 82 (T to G) to change the amino acid at 28 from Cys to Gly (SEQ ID NO:7).

Mammalian Expression of Receptor-ScFv-Fc fusion proteins. DNA constructs encoding the above cytokine receptor-ScFv-Fc fusion proteins were transiently transfected into CHO cells by lipofectamine/LIPO plus (Life Technologies) and supernatants were collected after 72 hours. Protein expression was measured by Western blotting with anti-human Fc HRP-conjugated antibody (Promega) and visualized by ECL (Pierce).

Affinity Measurements by BIAcore. The affinity of the various cytokine receptor-scFv fusion proteins for human IL-18 was measured using a BIAcore 2000. Receptor-scFv fusion proteins present in the CHO supernatant were captured onto the chip surface using anti-human Fc antibodies. Various concentrations of human IL-18 were injected over the surface and the time course of association and dissociation was monitored. Kinetic analysis using BIA evaluation software was performed to obtain the association and dissociation rate constants.

Results. The results are shown in Table 1 below. All of the receptor-scFv-Fc fusions exhibited increased affinity over that of each component separately. The fusions with the Fc domain at the C-terminus exhibited an approximately 4-fold higher affinity for hIL-18 than the anti-hIL-18 ScFv alone and an approximately 75-fold higher affinity for hIL-18 than the hIL-18Rα alone. The fusions with the Fc domain in between the hIL-18Rα and the anti-hIL-18 scFv exhibited a 2-fold and 75-fold increase in affinity over the anti-hIL-18 scFv alone or the hIL-18Rα alone, respectively.

TABLE 1

| | KD (pM) | off rate $s^{-1}$ | on rate $M^{-1} s^{-1}$ |
|---|---|---|---|
| anti-hIL18 ScFv-Fc | 193 | $4.65 \times 10^{-5}$ | $2.41 \times 10^5$ |
| hIL18Rα-Fc | 4180 | $6.53 \times 10^{-3}$ | $1.56 \times 10^6$ |
| hIL18Ra-anti-hIL18 ScFv-Fc | 53 | $2.12 \times 10^{-5}$ | $4 \times 10^5$ |
| anti-hIL18 ScFv-hIL18Rα-Fc | 42 | $1.61 \times 10^{-5}$ | $3.87 \times 10^5$ |
| hIL18Rα-Fc-anti-hIL18 ScFv | 92 | $3.70 \times 10^{-5}$ | $4.04 \times 10^5$ |
| anti-hIL18 ScFv-Fc-hIL18Rα | 137 | $3.90 \times 10^{-5}$ | $2.85 \times 10^5$ |

Example 2

IL-6 Traps: ScFv-ScFv Constructs

Generation of anti-IL-6 antibodies. Mice (Balb/c) were immunized with human IL-6 (hIL-6) protein (Regeneron Pharmaceuticals, Inc., New York) in adjuvant once every three weeks for a total of three injections followed by a boost with hIL-6 one month later. Approximately 2 weeks later, the spleen cells from one mouse were fused with myeloma cells by electrofusion. After fusion, the hybridoma cells were grown as a pool, and then plated as single cells in 96-well plates. A primary screen for the presence of monoclonal antibodies specific for IL-6 was performed on the hybridoma cell supernatant by two different ELISA methods. In one format, the hIL-6 was coated directly onto microtiter plates, incubated with the hybridoma cell supernatant and the presence of positive antibodies was visualized with anti-mouse IgG-HRP conjugated antibodies. The second format utilized a biotinylated hIL-6 that was captured onto the surface of microtiter plates coated with neutravidin. The hybridoma cell supernatant was incubated in the wells and the presence of positive antibodies was visualized with anti-mouse IgG-HRP conjugated antibodies. Hybridoma cell supernatant was considered positive i.e., contained anti-hIL-6 monoclonal antibodies, if the OD at 450 nm was equal or greater than 1.0 in either ELISA format.

Binding assays. Cell supernatant for hybridomas expressing monoclonal antibodies that scored positive on the primary screen were then assayed in secondary screens for total antibody concentration and apparent affinity by a binding assay. For the binding assay, hybridoma cell supernatant containing antibodies at a concentration of 1 nM were incubated for 3 hours at room temperature with varying concentrations of hIL-6. These mixtures were assayed for the presence of free antibody using the hIL-6 ELISA from the primary screen. An apparent $K_D$ can be calculated from the $IC_{50}$, the IL-6 concentration at which half of the antibody is free. Based on this analysis, five hybridomas were chosen for cell cloning by limiting dilution.

Epitope analysis. Supernatant from 25 positive hybridomas from the primary and secondary screens were further analyzed by Bia-MAP and antibody competition assays to identify classes of antibodies that recognize different epitopes on hIL-6. The monoclonal antibodies grouped into 4 classes, with one class subdivided into 5 groups. Based on these data, 5 additional hybridoma cells representing antibodies from the different classes were chosen for 'limiting dilution' cloning.

Isolation of antibody variable regions. The variable region of the heavy chain ($V_H$) and the light chain ($V_L$) for each antibody was isolated from clonal hybridoma cells using rapid amplification of cDNA ends (RACE). Total RNA was isolated from ~2–5×10$^7$ hybridoma cells using Trizol reagent. The isotype for each of the monoclonal antibodies was determined and isotype-specific primers within the constant region of the $V_H$ and $V_L$ were utilized to synthesize the 1$^{st}$ strand cDNA from total RNA. This cDNA was then tailed with polyG using terminal transferase and the variable regions were then amplified by PCR using a polyC primer and a second set of isotype-specific primers nested to the original set. The amplification product was then cloned and sequenced. The $V_H$ and $V_L$ for each antibody was constructed into a scFv format by PCR using standard techniques to insert a stretch of nucleotides between the 3' end of the $V_H$ and the 5' end of the $V_L$ that would encode for 15 amino acids, $(G_4S)_3$ (SEQ ID NO:2) as well as add nucleotides carrying restriction sites at the 5' end of the $V_H$ and 3' end of the $V_L$ for ease of cloning.

Construction of ScFv-ScFv-Fc fusions. All combinations of scFvs (having mono- or multispecificity) were constructed in a mammalian expression vector by restriction enzyme subcloning to generate two ScFvs in tandem separated by nucleotide sequence SEQ ID NO:1 between the two scFvs followed by the coding region of Fc domain of human IgG1. DNA constructs encoding various scFv-scFv-Fc fusion proteins were transiently transfected into CHO cells by lipofectamine (Life Technologies) by standard techniques and supernatants were collected after 72 hours. Protein expression was measured by Western blotting with anti-human Fc HRP-conjgated antibody (Promega) and visualized by ECL (Pierce).

Affinity Measurements. The affinity of the various scFv-scFv-Fc fusion proteins for human IL-6 was measured using a BIAcore 2000. ScFv-scFv-Fc fusion proteins present in the CHO cell supernatant from transient transfection were captured onto the chip surface that had been coated with anti-human Fc antibodies. Between 300–700 Resonance Units (RUs) were captured. After capture, various concentrations of hIL-6 (1.25 nM, 2.5 nM and 5 nM) were injected over the surface and the time course of association and dissociation was monitored. Kinetic analysis using BIAevaluation software was performed to obtain the association and dissociation rate constants. The results are shown in Table 2.

TABLE 2

| Construct | ScFv | Kd | Fold Increase (from position 1) | Fold Increase (from position 2) |
|---|---|---|---|---|
| ScFv-Fc | 8F10 (SEQ ID NO: 9) | 430 pM | | |
| | 3D6 (SEQ ID NO: 10) | 1.2 nM | | |
| | 6E2 (SEQ ID NO: 11) | 608 pM | | |
| | 5A11 (SEQ ID NO: 12) | 1.5 nM | | |
| ScFv-ScFv-Fc | 8F10.8F10 | 296 pM | | |
| | 3D6.3D6 | 3.3 nM | | |
| | 6E2.6E2 | 651 pM | | |
| | 3D6.3D6 | 3.1 nM | | |
| | 6E2.3D6 | 85 pM | 7.7 | 38.8 |
| | 3D6.6E2 | 30 pM | 110.0 | 21.7 |
| | 8F10.6E2 | 5.1 pM | 58.0 | 127.6 |
| | 6E2.8F10 | 28.0 pM | 23.3 | 10.6 |
| | 5A11.6E2 | 81 pM | 38.3 | 8.0 |
| | 6E2.5A11 | 92 pM | 7.1 | 33.7 |
| | 5A11.8F10 | 49 pM | 63.3 | 6.0 |
| | 5A11.3D6 | 16 pM | 193.8 | 206.3 |

What is claimed is:

1. An isolated nucleic acid encoding a soluble interacting protein (SIP)-specific fusion polypeptide, wherein the fusion polypeptide comprises:

a) one or more components which comprise a SIP binding domain of a SIP target binding domain (TBD);

b) one or more components which comprise a SIP binding domain of an immunoglobulin (IBD); and c) a multimerizing component (M), wherein M multimerizes with M on another fusion polypeptide to form a multimer of the fusion polypeptides.

2. The isolated nucleic acid of claim 1, wherein M comprises a constant region(s) of an immunoglobulin or derivative thereof.

3. The isolated nucleic acid of claim 2, wherein M is selected from the group consisting of the Fc domain of the heavy chain of IgG, and the heavy chain hinge $C_H2$ and $C_H3$ constant regions.

4. The isolated nucleic acid of claim 1, wherein M is an amino acid sequence of 1 to about 200 amino acids in length having at least one cysteine residue.

5. The isolated nucleic acid of claim 1, wherein M comprising the IBD is selected from the group consisting of a heavy chain variable domain, a light chain variable domain and an ScFv.

6. The isolated nucleic acid of claim 1, wherein the one or more components are (i) connected directly to each other or (ii) are connected to each other by one or more spacer molecules, or (iii) are connected with a combination of (i) and (ii).

7. The isolated nucleic acid of claim 6, wherein one or more component domain(s) is(are) connected to another component domain with a peptide of about 1–100 amino acids.

8. The isolated nucleic acid of claim 1 further comprising a signal sequence at the amino terminal end of the SIP-specific fusion protein.

9. The isolated nucleic acid of claim 8, wherein the SIP-specific fusion polypeptide component arrangements are selected from the group consisting of:

a) $(TBD)_x$-$(IBD)_y$-M;

b) $(TBD)_x$-M-$(IBD)_y$;

c) $(IBD)_x$-$(TBD)_y$-M;

d) SS-$(TBD)_x$-$(IBD)_y$-M; and e) SS-$(IBD)_x$-$(TBD)_y$-M;

wherein SS is a signal sequence, and $x \geqq 1$ and $y \geqq 1$.

10. The isolated nucleic acid of claim 9, wherein the SIP-specific fusion polypeptide has the arrangement $(IBD)_x$-$(TBD)_y$-M, wherein x=1 and y=1.

11. A fusion polypeptide encoded by the nucleic acid molecule of claim 1.

12. A trapbody which is a dimer comprising two of the fusion polypeptides of claim 11.

13. A method of producing a SIP-specific fusion polypeptide, comprising culturing a host cell transfected with a vector comprising the nucleic acid of claim 1, under conditions suitable for expression of the protein from the host cell, and recovering the fusion protein so produced.

14. A pharmaceutical composition comprising the trapbody of claim 12 and a pharmaceutically acceptable carrier.

* * * * *